US00PP13550P2

(12) United States Plant Patent
Hoek

(10) Patent No.: US PP13,550 P2
(45) Date of Patent: Feb. 4, 2003

(54) CHRYSANTHEMUM PLANT NAMED 'ANASTASIA'

(75) Inventor: Jan Hoek, 's-Gravenzande (NL)

(73) Assignee: Deliflor Chrysanten B.V., Maasdijk (NL)

( * ) Notice: Subject to any disclaimer, the term of this patent is extended or adjusted under 35 U.S.C. 154(b) by 0 days.

(21) Appl. No.: 09/968,331

(22) Filed: Sep. 30, 2001

(51) Int. Cl.[7] ..... A01H 5/00

(52) U.S. Cl. ..... Plt./288

(58) Field of Search ..... Plt./288

*Primary Examiner*—Howard J. Locker
(74) *Attorney, Agent, or Firm*—C. A. Whealy

(57) ABSTRACT

A distinct cultivar of Chrysanthemum plant named 'Anastasia', characterized by its large quilled spider double-type inflorescences with white ray florets; numerous ray florets and few inconspicuous disc florets; dark green foliage; strong flowering stems; low number of lateral branches; short response time; and excellent postproduction longevity.

2 Drawing Sheets

BACKGROUND OF THE INVENTION

The present invention relates to a new and distinct cultivar of Chrysanthemum plant, botanically known as *Chrysanthemum×morifolium* and referred to by the name 'Anastasia'.

The new Chrysanthemum originated from a cross made by the Inventor in the Autumn of 1998, in 's-Gravenzande, The Netherlands, of the Chrysanthemum cultivar Spider White, not patented, as the female, or seed, parent with a proprietary Chrysanthemum selection identified as code number 93411, as the male, or pollen, parent. Seed from the cross was sown in March, 1999, and the cultivar Anastasia was discovered and selected by the Inventor within the progeny of the stated cross in a controlled environment in 's-Gravenzande, The Netherlands, on or about Jun. 25, 1999. The selection of this plant was based on its inflorescence form, color and good substance.

Asexual reproduction of the new Chrysanthemum by terminal cuttings harvested in 's-Gravenzande, The Netherlands, since August 1999, has shown that the unique features of this new Chrysanthemum are stable and reproduced true to type in successive generations.

BRIEF SUMMARY OF THE INVENTION

The cultivar Anastasia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Anastasia'. These characteristics in combination distinguish 'Anastasia' as a new and distinct cultivar:

1. Large quilled spider double-type inflorescences with white ray florets; typically grown as a disbudded type, a single inflorescence per flowering stem.

2. Numerous ray florets and few disc florets; disc florets typically inconspicuous.

3. Dark green foliage.

4. Strong flowering stems.

5. Low number of lateral branches which reduces the amount of disbudding required.

6. Short response time.

7. Excellent postproduction longevity.

Plants of the new Chrysanthemum can be compared to plants of the male parent, the cultivar Spider White. In side-by-side comparisons conducted by the Inventor in 's-Gravenzande, The Netherlands, plants of the new Chrysanthemum differed from plants of the cultivar Spider White in the following characteristics:

1. Plants of the new Chrysanthemum developed fewer lateral inflorescences than plants of the cultivar Spider White.

2. Plants of the new Chrysanthemum had darker green and broader leaves than plants of the cultivar Spider White.

3. Leaves of plants of the new Chrysanthemum had shorter petioles than leaves of plants of the cultivar Spider White.

4. Plants of the new Chrysanthemum flowered about one week earlier than plants of the cultivar Spider White.

5. Disc florets of plants of the new Chrysanthemum were inconspicuous whereas the disc florets of plants of the cultivar Spider White were conspicuous.

Plants of the new Chrysanthemum can also be compared to plants of the female parent, the selection 93411. In side-by-side comparisons conducted by the Inventor in 's-Gravenzande, The Netherlands, plants of the new Chrysanthemum and the selection 93411 differed in the following characteristics:

1. Plants of the new Chrysanthemum had longer flowering stems than plants of the selection 93411.

2. Plants of the new Chrysanthemum had darker green and larger leaves than plants of the selection 93411.

3. Ray florets of plants of the new Chrysanthemum were quilled whereas ray florets of plants of the selection 93411 were incurved.

4. Inflorescences of plants of the new Chrysanthemum developed few disc florets whereas inflorescences of plants of the selection 93411 developed many disc florets.

5. Plants of the new Chrysanthemum did not produce as much pollen as plants of the selection 93411.

Plants of the new Chrysanthemum are similar to plants of the cultivar Delistar, disclosed in U.S. Plant patent application Ser. No. 11,964. In side-by-side comparisons conducted by the Inventor in 's-Gravenzande, The Netherlands, plants of the new Chrysanthemum and the cultivar Delistar differed in the following characteristics:

1. Stem color of plants of the new Chrysanthemum was slightly darker than stem color of plants of the cultivar Delistar.

2. Leaf color of plants of the new Chrysanthemum was darker than leaf color of plants of the cultivar Delistar.

3. Ray florets of plants of the new Chrysanthemum were longer and broader than ray florets of the cultivar Delistar.

4. Inflorescences of plants of the new Chrysanthemum were larger and had more ray florets than inflorescences of plants of the cultivar Delistar.

5. Plants of the new Chrysanthemum had shorter and thicker peduncles than plants of the cultivar Delistar.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Chrysanthemum.

The photograph on the first sheet comprises a side perspective view of a typical flowering stem of 'Anastasia'.

The photograph at the top of the second sheet comprises a close-up view of a typical inflorescence of 'Anastasia'.

The photograph at the bottom of the second page comprises a close-up view of the upper and lower surfaces of typical leaves of 'Anastasia'.

DETAILED BOTANICAL DESCRIPTION

In the following description, color references are made to The Royal Horticultural Society Colour Chart except where general terms of ordinary dictionary significance are used. The aforementioned photographs, following observations and measurements describe plants grown in 's-Gravenzande, The Netherlands, under commercial practice in a glass-covered greenhouse. Plants were initially given short nyctoperiods followed by long nyctoperiods to induce flower initiation and development. Average day and night temperatures were 18 and 19° C., respectively. Plants were grown as single-stem disbud types.

Botanical classification: *Chrysanthemum×morifolium* cultivar Anastasia.

Commercial classification: Quilled spider double-type Chrysanthemum typically grown as a disbudded cut flower.

Parentage:

*Female or seed parent.*—*Chrysanthemum×morifolium* cultivar Spider White, not patented.

*Male or pollen parent.*—Proprietary *Chrysanthemum×morifolium* selection identified as code number 93411.

Propagation:

*Type.*—Terminal tip cuttings.

*Time to initiate roots, summer.*—About 10 days at 20° C.

*Time to initiate roots, winter.*—About 14 days at 20° C.

*Root description.*—Fine, fibrous and well-branched.

Plant description:

*Appearance.*—Herbaceous quilled spider double-type cut Chrysanthemum; typically grown as a single-stem and as a disbudded type with one single inflorescence per flowering stem. Upright with strong stems.

*Growth rate.*—Moderate; moderately vigorous.

*Crop time.*—For cut flowers, about 78 and 117 days are required to produce flowering stems during the summer and winter, respectively.

*Flowering stem description.*—Length: About 70 to 80 cm. Diameter, at apex: About 6.5 mm. Strength: Strong. Aspect: Upright. Branching habit: Plants are typically grown as single stems, but if pinched, will develop 8 to 12 lateral stems. Color: 146B.

*Foliage description.*—Arrangement: Alternate. Quantity of leaves per main stem: About 12 to 15. Length: About 11.5 cm. Width: About 7.5 cm. Apex: Acute. Base: Acute to obtuse. Margin: Palmately lobed. Texture: Rough; both surfaces pubescent. Petiole length: About 3.5 cm. Color: Young and fully expanded foliage, upper surface: 147A. Young and fully expanded foliage, lower surface: 147B. Venation, upper and lower surfaces: 147B. Petiole: 147B.

Inflorescence description:

*Appearance.*—Quilled spider double-type inflorescence form. Inflorescence borne on terminals, arising from leaf axils. Ray and disc florets arranged acropetally on the receptacle.

*Flowering response.*—Under natural conditions, plant typically flowers in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about seven weeks later.

*Postproduction longevity.*—Inflorescences will maintain good substance and form for about 3.5 weeks after harvesting.

*Quantity of inflorescences per flowering stem.*—Grown as a disbud type, all lateral inflorescences are removed and only the terminal inflorescence develops. If lateral inflorescences are not removed, about 8 to 11 inflorescences per flowering stem will develop.

*Inflorescence size.*—Diameter: Large, about 12.5 cm. Depth (height): About 4.5 cm. Diameter of disc: About 1.4 cm; inconspicuous.

*Inflorescence buds.*—Length: About 1.25 cm. Diameter: About 1.35 cm. Shape: Flattened sphere. Color: Greenish white (no color similar in R.H.S. Colour Chart).

*Ray florets.*—Length, fully developed: About 7 cm. Width, fully developed: About 7.5 mm. Shape: Fused, tubular; quilled. Texture: Smooth, glabrous. Number of ray florets per inflorescence: About 350. Color: When opening, upper and lower surfaces: 155B. Mature, upper and lower surfaces: Lighter than 155D.

*Disc florets.*—Shape: Oblong, tubular. Length: About 5 mm. Width: About 1 mm. Number of disc florets per inflorescence: Few, about 10; inconspicuous. Color: Immature: Greenish white (no color similar in R.H.S. Colour Chart). Mature: Towards apex, 13A;

towards base, greenish white (no color similar in R.H.S. Colour Chart).

*Peduncles.*—Length, terminal peduncle: About 3.5 cm. Length, fourth peduncle: About 4.5 cm. Diameter: About 6.5 mm. Angle: About 60 to 80° to main stem. Texture: Pubescent. Color: 146B.

*Reproductive organs.*—Androecium: Present on disc florets only. Anther color: 15B. Amount of pollen: Moderate. Pollen: 16B. Gynoecium: Present on both ray and disc florets. Stigma length: About 5 mm. Stigma width: About 0.5 mm. Stigma color: Towards apex, 9C; towards base, close to 155C.

*Seed.*—Seed production has not been observed.

Disease/pest resistance: Resistance to known Chrysanthemum pathogens and pests has not been observed on plants of the new Chrysanthemum.

It is claimed:

1. A new and distinct cultivar of Chrysanthemum plant named 'Anastasia', as illustrated and described.

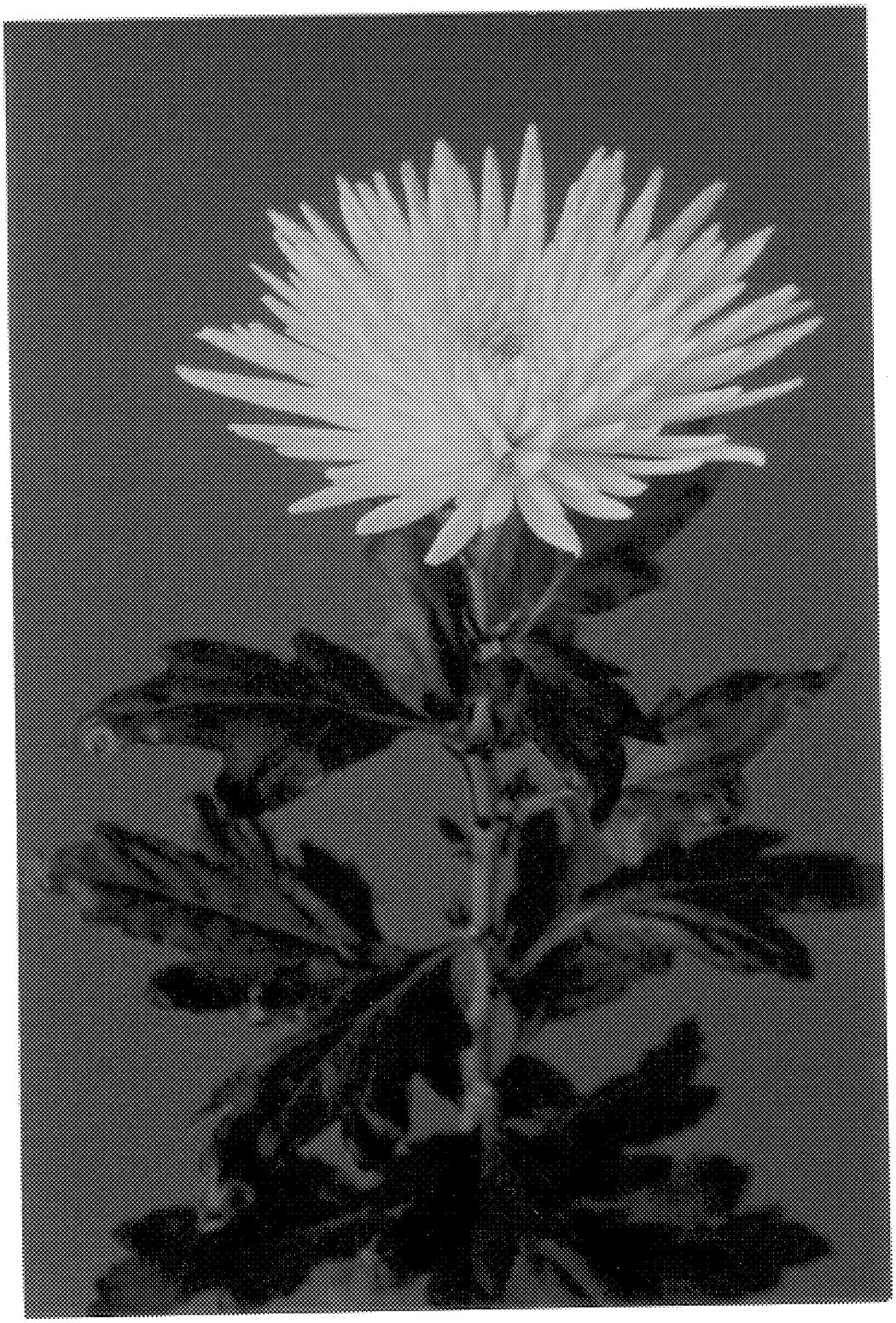

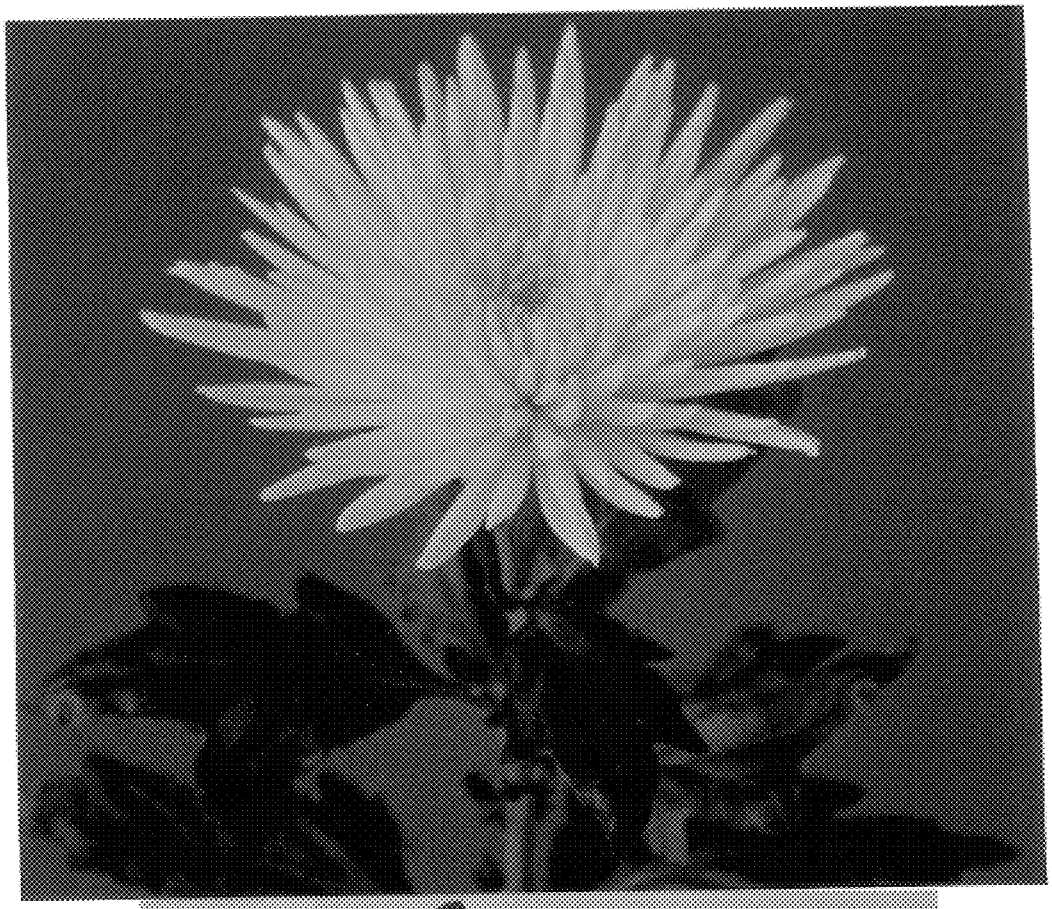
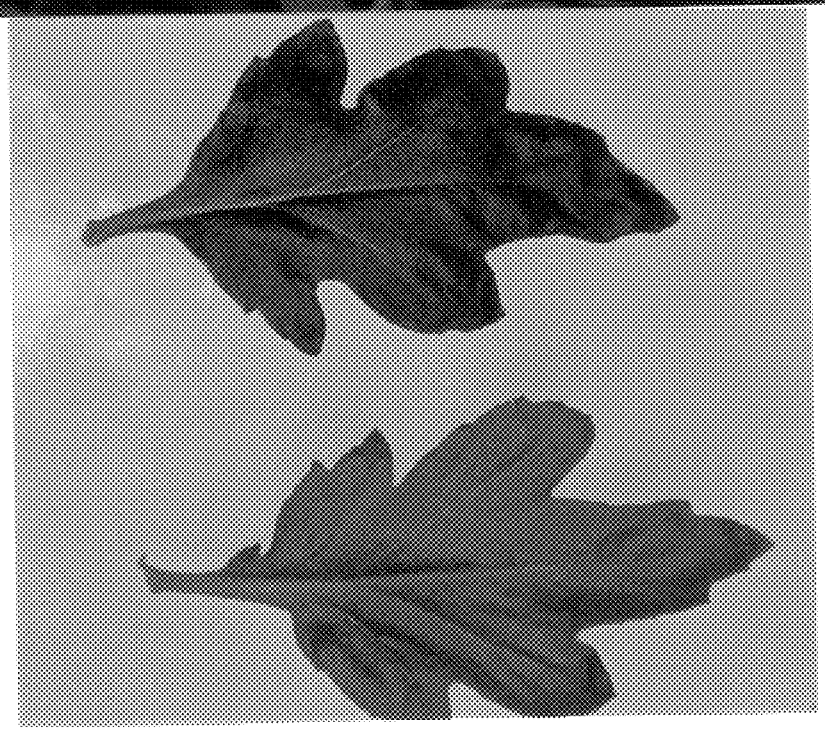

* * * * *